(12) United States Patent
Nakao

(10) Patent No.: US 6,929,601 B2
(45) Date of Patent: Aug. 16, 2005

(54) ENDOSCOPIC SHEATH ASSEMBLY AND ASSOCIATED METHOD

(75) Inventor: Naomi Nakao, New York, NY (US)

(73) Assignee: Granit Medical Innovation LLC, New York, NY (US)

( * ) Notice: Subject to any disclaimer, the term of this patent is extended or adjusted under 35 U.S.C. 154(b) by 71 days.

(21) Appl. No.: 10/414,708

(22) Filed: Apr. 16, 2003

(65) Prior Publication Data

US 2004/0210110 A1 Oct. 21, 2004

(51) Int. Cl.[7] ................................................. A61B 1/00
(52) U.S. Cl. ........................ 600/121; 600/124; 600/125
(58) Field of Search ................................. 600/121–125

(56) References Cited

U.S. PATENT DOCUMENTS 4,886,049 A * 12/1989 Darras ........................ 600/124
5,217,001 A * 6/1993 Nakao et al. ................ 600/123
5,337,731 A * 8/1994 Takahashi et al. ........... 600/109
5,503,616 A * 4/1996 Jones .......................... 600/153

* cited by examiner

Primary Examiner—Beverly M. Flanagan
(74) Attorney, Agent, or Firm—R. Neil Sudol; Henry D. Coleman; William J. Sapone

(57) ABSTRACT

An endoscope sheath includes a web member disposable in a tubular configuration in engagement with an endoscope insertion member, the member being provided with a tear string in the form of a tensile member. The tear string preferably extends longitudinally along the web member. In addition, the tear string preferably extends from one end of the web member to an opposite end thereof and is disposed along a weakened area of the web member. The web member is provided in a plurality of regions with a layer of adhesive material. The adhesive material of at least one of the regions is permanent adhesive, whereas the adhesive material of at least another of the regions forms a separable bond. These regions extend along opposing longitudinal edges of the web member.

22 Claims, 4 Drawing Sheets

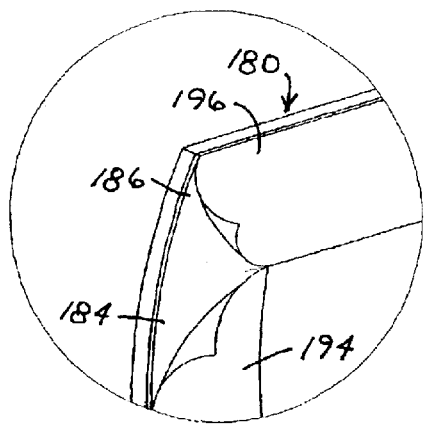
FIG. 3
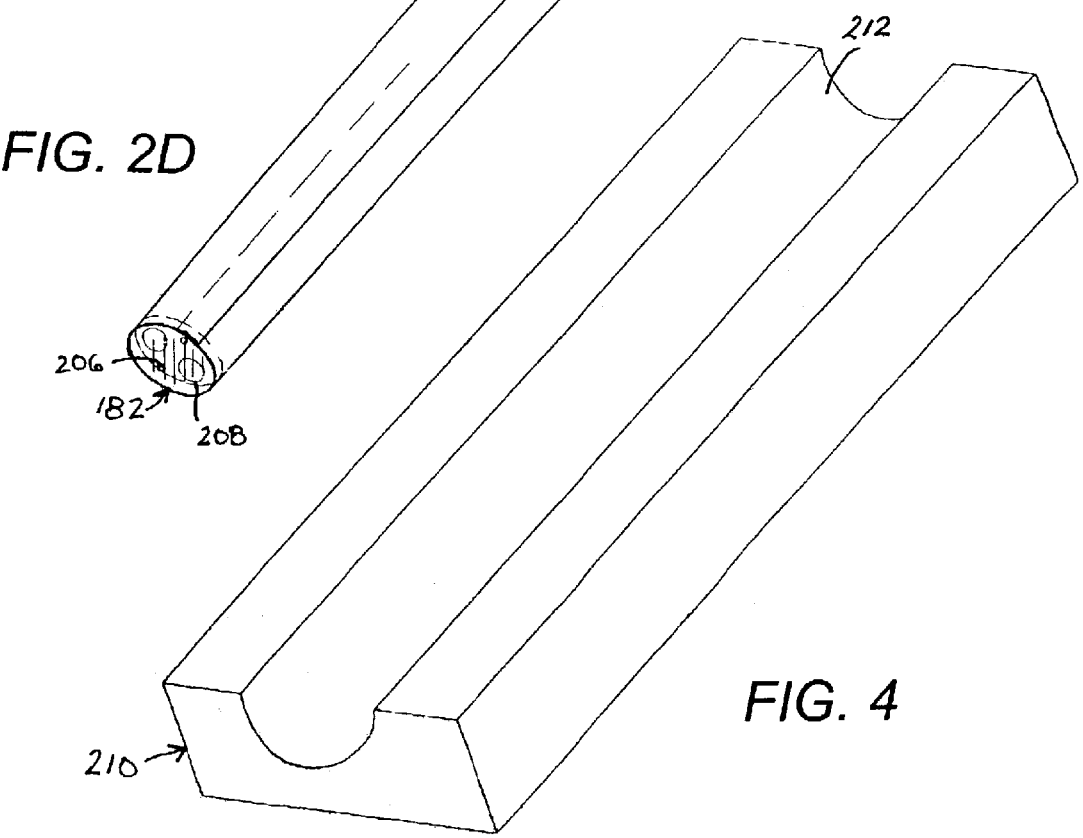
FIG. 2D
FIG. 4

ENDOSCOPIC SHEATH ASSEMBLY AND ASSOCIATED METHOD

BACKGROUND OF THE INVENTION

This invention relates to a medical device and to an associated medical technique. More particularly, this invention relates to an endoscopic sheath assembly and to an associated endoscopic method.

Flexible endoscopes are inserted into the digestive tract for diagnostic and therapeutic purposes. Endoscopes generally include a light guide for transmitting optical-wavelength electromagnetic radiation into the patient. Images are captured, typically via lenses and an optical fiber bundle or a charge-coupled device, whereby a user can visually inspect the inner walls or surfaces of the digestive tract. One common objective of endoscopic investigations in the digestive tract is to detect the presence of polyps. Where a polyp is visually detected, particularly in the colon, it should be severed, captured, and removed from the patient. Alternatively, particularly where the polyp may be a malignant cancer, the polyp may be severed and captured for extraction from the patient.

One problem in endoscopy is the potential for the transmission of infection from one patient to another because of remaining bioburden inside or on the endoscope. Traditionally, this problem is countered by thoroughly cleaning the instrument. However, it is difficult to adequately clean an endoscope, particularly the biopsy channel thereof. One solution has been to encase the endoscope insertion member in a disposable sheath which is sealed to prevent the accumulation of bioburden inside or on the endoscope. Such a sheath is made of a very delicate thin material and is long, flimsy and very narrow. To securely apply the sheath to an endoscope without ripping the sheath is difficult. Removing a sheath from an endoscope without contaminating the endoscope is also difficult.

OBJECTS OF THE INVENTION

It is a general object of the present invention to provide an improved endoscope sheath or sheath assembly.

A further object of the present invention is to provide such a sheath which is inexpensive and/or easy to use.

It is an even more specific object of the present invention to provide such a sheath which is particularly suitable for use with flexible endoscopes during investigations of the digestive or gastro-intestinal tract and which may be used in investigations of any internal body cavity.

A further objective is to minimize the amount of time it takes to reprocess an endoscope between successive procedures.

These and other objects of the invention will be apparent from the drawings and descriptions herein. Although every object of the invention is attained by at least one embodiment of the invention, there is not necessarily any one embodiment that achieves all of the objects of the invention.

SUMMARY OF THE INVENTION

An endoscope sheath in accordance with the present invention includes a web member disposable in a tubular configuration in engagement with an endoscope insertion member, the member being provided with a tear string in the form of a tensile member. The tear string preferably extends longitudinally along the web member. In addition, the tear string preferably extends from one end of the web member to an opposite end thereof and is preferably disposed along a weakened area of the sheath to facilitate the severing of the sheath by the tear string.

The sheath is preferably provided with an end cap securable over a distal tip of the endoscope insertion member in a fluid tight engagement with the web member. The end cap is secured or securable to an end of the web member.

Pursuant to another feature of the present invention, the web member is provided in at least one region with a layer of adhesive material. The adhesive material of that region is preferably permanent adhesive. Optionally, the web member may be provided in one or more additional regions with a layer of adhesive material. The adhesive material of these other regions forms a separable bond. In one embodiment of the invention, two adhesive regions extend along opposing longitudinal edges of the web member, at least where web member is a rectangular sheet.

A medical method in accordance with the present invention comprises providing an endoscope insertion member, providing a sheath in the form of a web or sheet, wrapping the sheath about at least a distal end portion of the insertion member, adhesively fastening the sheath about the insertion member, inserting the insertion member with the sheath wrapped thereabout into a patient, and subsequently removing the insertion member with the sheath wrapped thereabout from the patient. The sheath may then be removed from the endoscope insertion member, for instance, by pulling a tear string embedded in the sheath to sever the sheath along a predetermined line where the sheath is weakened (e.g., a score line), and subsequently separating the insertion member and the torn or severed sheath from one another.

The fastening of the sheath may include removing at least one protective cover strip from the sheath to uncover at least one adhesive region and subsequently pressing the adhesive region against the insertion member. After the wrapping of the sheath about the endoscope insertion member, the adhesive region is placed into contact with an outer surface of the sheath and pressed against the endoscope insertion member. This adhesive layer preferably forms a permanent bond. Where the sheath is provided in another region with a layer of nonpermanent adhesive, this region is placed into direct contact with the sheath. Subsequently, a portion of the sheath bearing the permanent adhesive layer is wrapped over the region in direct contact with the sheath.

The wrapping of the sheath includes, pursuant to a preferred feature of the invention, providing a cradle member having a groove, placing the web or sheet over the cradle member so that a portion of the web or sheet lies in the groove, disposing the endoscope insertion member on the portion of the web or sheet lying in the groove, and winding a side portion of the web or sheet about the endoscope insertion member after the disposing thereof on the web or sheet. This technique facilitates application of the sheath in that the endoscope insertion member is partially surrounded by the sheath in the cradle member and the operator or user need only fold the longitudinal edge portions over one another and press the adhesive regions to effectuate an effectively secure closure.

The fastening of the sheath to the endoscope insertion member may include, pursuant to a particular feature of the present invention, adhesively securing a first longitudinal edge region of the web or sheet to an outer surface of the endoscope insertion member, and subsequently adhesively securing a second longitudinal edge region of the web or sheet to on outer surface of the web or sheet.

The sheath may include built-in or insertable biopsy, suction and irrigation channels or any combination thereof or may include space along the length of the sheath to allow addition of said channels which may be comprised of tubing.

BRIEF DESCRIPTION OF THE DRAWINGS

FIG. 3 is a detail schematic isometric view of a portion III of the sheath of FIG. 2A, on a larger scale.

FIG. 4 is a schematic isometric view of a support, in accordance with the present invention, for an endoscope insertion member, to aid in the application process of FIGS. 2A–2D.

DETAILED DESCRIPTION OF THE PREFERRED EMBODIMENTS

Figure 1:
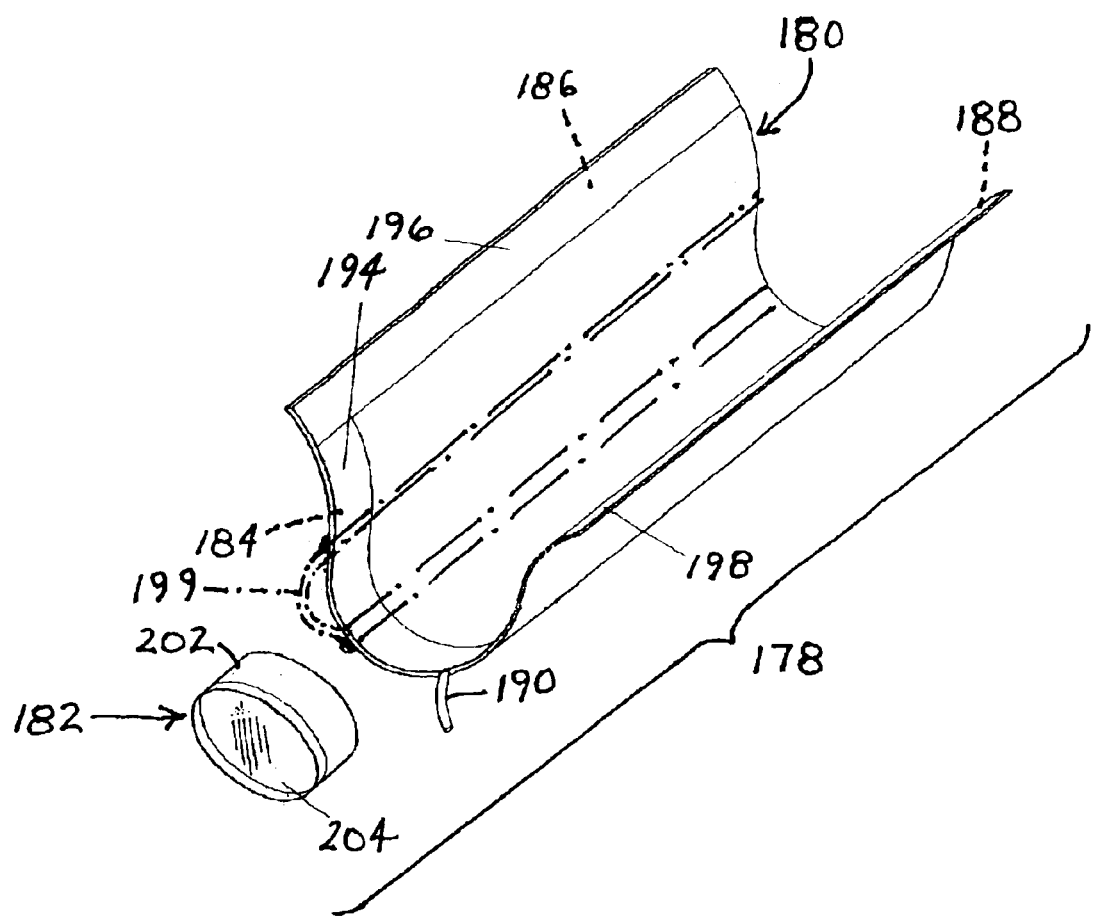
FIG. 1 is a schematic exploded isometric view of an endoscopic sheath assembly in accordance with the present invention utilizable in the procedures of FIGS. 8A–8H and 9A–9H.
Figure 2:
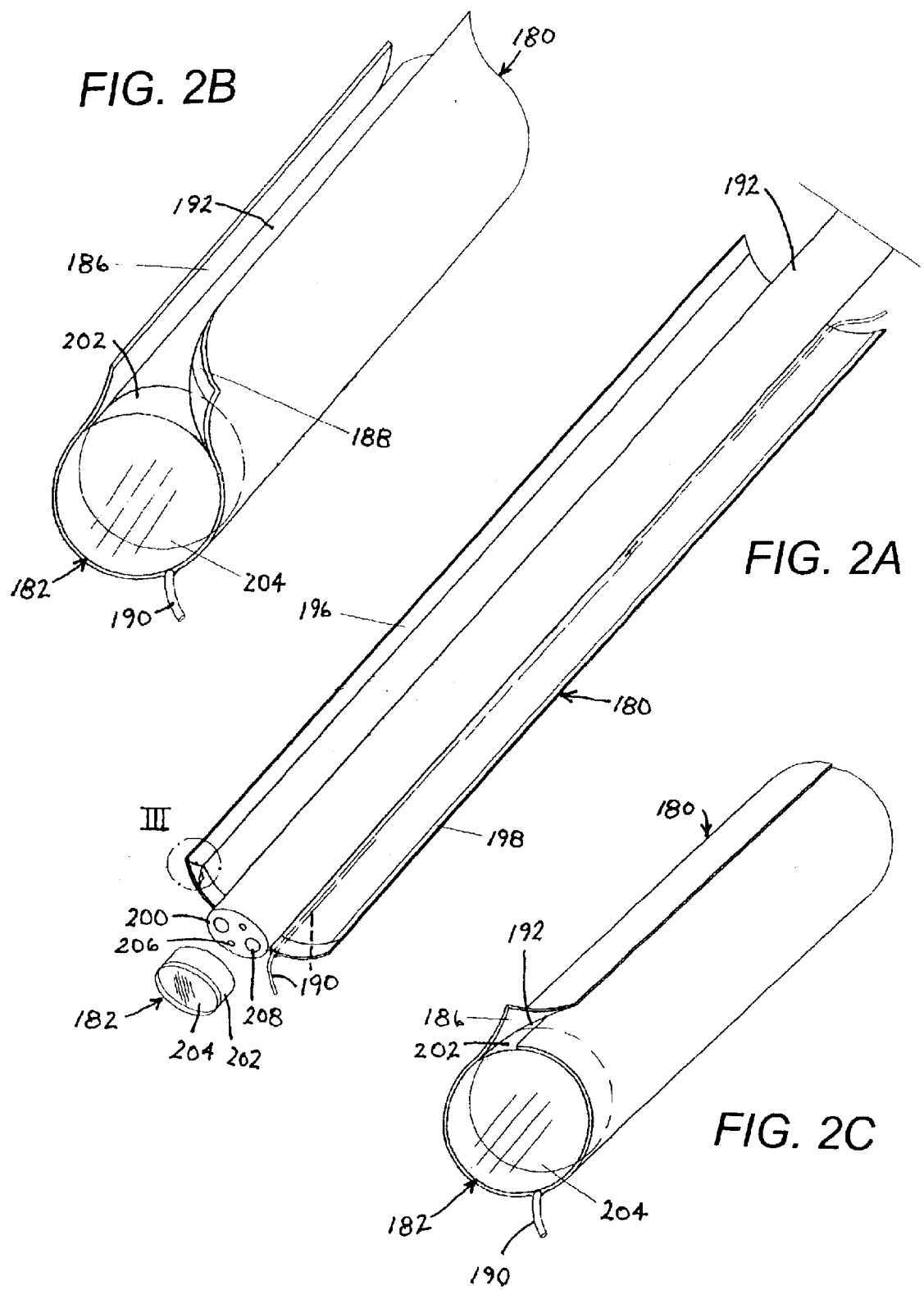
FIGS. 2A–2D are schematic isometric views of an endoscopic insertion shaft and the sheath assembly of FIG. 1, showing successive steps in the application of the sheath assembly to the endoscope insertion shaft, in accordance with the present invention.

As depicted in FIG. 1, an endoscopic sheath assembly 178 includes an endoscope sheath 180 in the form of a web member or sheet and further includes an endoscope end cap 182. Sheath 180 is provided with a layer of adhesive material 184, 186, 188 along a forward end region, a first longitudinal edge region and a second longitudinal edge region, respectively (not separately enumerated). Sheath 180 is further provided along an elongate weakened (e.g., thinned or scored) region (not separately labeled) with an embedded tensile member 190 such as a tear string for enabling a severing of the sheath in preparation for removal of the sheath from an endoscope insertion member 192 (FIG. 2A). Releasable protective cover strips 194, 196, 198 are removably attached to the adhesive layers or regions 184, 186, 188. Preferably, the adhesive material of layers or regions 184 and 186 is a permanent adhesive, while the adhesive material of layer or region 188 forms a separable or releasable bond. Optionally, sheath 180 includes one or more built-in or insertable biopsy, suction and irrigation channels 199 or may include space along the length of the sheath to allow addition of said channels which may be comprised of tubing.

In applying endoscopic sheath assembly 178 to endoscope insertion member 192 (FIG. 2A), end cap 182 is first placed over a distal tip 200 of the insertion member. End cap 182 includes a substantially rigid collar 202 and a transparent plate 204. End plate 204 transmits illumination into a patient from a light outlet 206 on endoscope tip 200. Returning light passes through plate 204 and impinges on a lens 208.

After the placement of end cap 182 over distal tip 200 of insertion member 192, protective cover strip 198 is peeled away from longitudinal adhesive layer 188. In addition, protective cover strip 194 (see FIG. 3) is removed from adhesive layer 184. Adhesive layer 188 is aligned longitudinally with endoscope insertion member 192 with the latter in a straight configuration, parallel to an axis thereof. Adhesive layer 188 is pressed against insertion member 192. Then the distal end of sheath or web member 180 is wrapped around collar 202, as shown in FIG. 2B, so that adhesive layer 184 permanently bonds to end cap 182. Prior to completing the wrapping of the distal end of sheath or web member 180 about collar 202, protective cover strip 196 is peeled away from longitudinal adhesive layer 186 (see FIG. 3). The uncovered layer 186 of permanent adhesive is then placed into an overlapping configuration with the sheath or web 180 and bonded thereto (FIG. 2C) so that the sheath surround the endoscope insertion member 192 in tight fluid-sealed fit (FIG. 2D).

An alternative method of applying sheath assembly 178 to endoscope insertion member 192 utilizes a support cradle 210 shown in FIG. 4. Support cradle 210 has a groove 212 of equivalent diameter to insertion member 192. First sheath or web member 180 with at least protective cover strip 194 removed is laid into groove 212. Endoscope insertion member 192 with end cap 182 positioned thereon is then placed atop sheath 180 so that collar 202 engages exposed adhesive layer 184. At this time, protective cover strip 198 may be removed to expose adhesive layer 188 which is then pressed along insertion member 192. Subsequently, strip 196 is removed to expose permanent-adhesive layer 186 which is then bonded to an outer surface of the sheath or web 180.

Figures 5, 6, 7, 8:
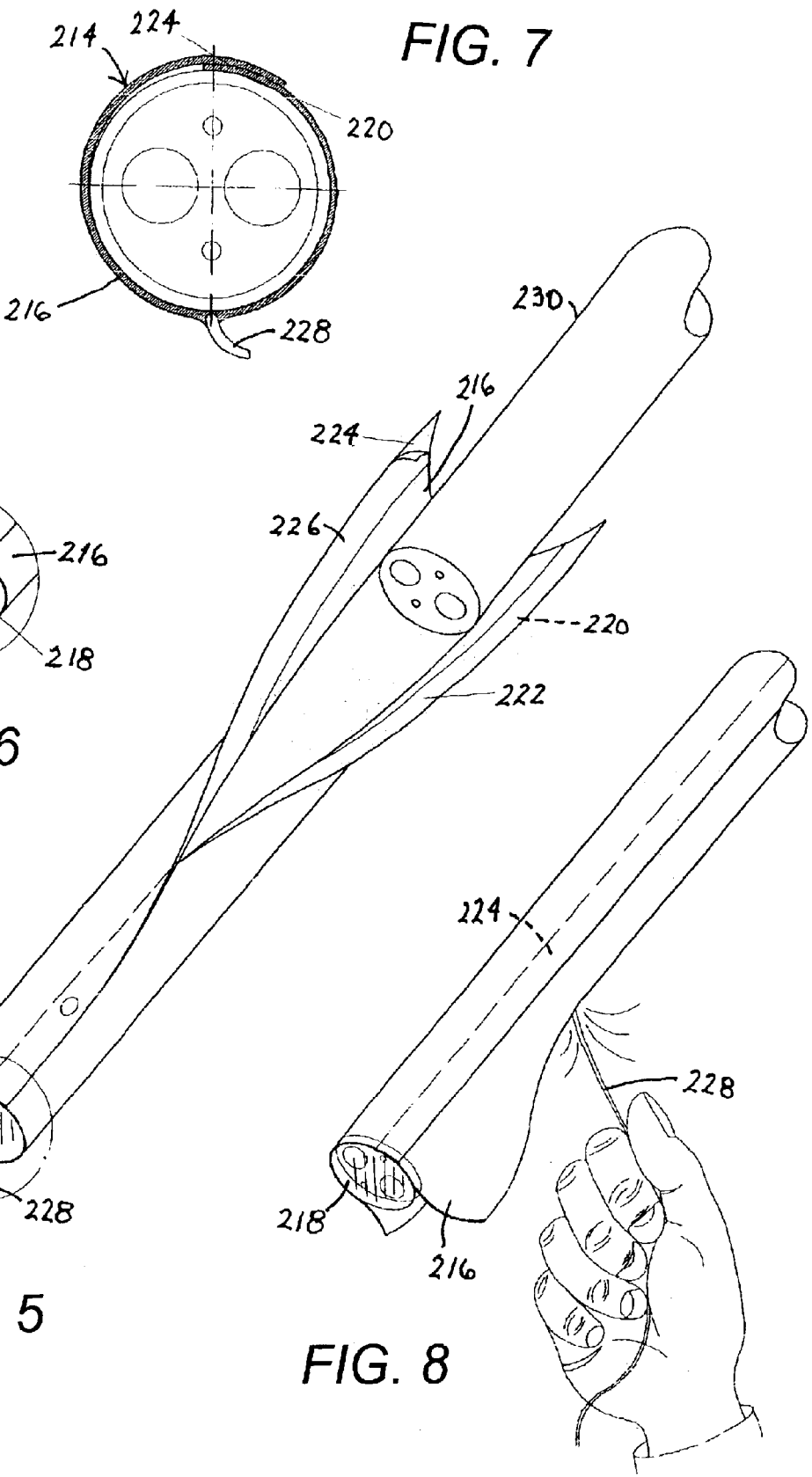
FIG. 5 is a schematic isometric view, of a modified endoscopic sheath assembly in accordance with the present invention, showing a step in the application of the sheath assembly to an endoscope insertion shaft.
FIG. 6 is a detail view, on a larger scale, of a distal end of the sheath assembly of FIG. 5.
FIG. 7 is a schematic end elevational view, on an even larger scale, of the sheath assembly of FIG. 5.
FIG. 8 is a schematic isometric view of a sheath assembly in accordance with the present invention on an endoscope insertion shaft, showing a stage in the removal of the sheath assembly from the endoscope insertion shaft.

In an alternative sheath assembly 214 shown in FIG. 5, a sheath or web member 216 is attached to an end cap 218 during manufacture. Sheath or web 216 is provided along part of a first longitudinal edge with a layer 220 of lightly bonding adhesive covered by a releasable protective strip 222. Sheath or web 216 is provided along part of a second or opposing longitudinal edge with a layer 224 of permanently bonding adhesive covered by a releasable protective strip 226. A tear string 228 is embedded in sheath or web 216 and extends longitudinally therealong. Along a distal end portion of sheath assembly 214, the opposing longitudinal edge regions of the sheath or web 216 overlap and are bonded to one another, prior to introduction of an endoscope insertion member 230 into the sheath assembly, as shown in FIGS. 5 and 16.

FIG. 8 depicts an initial step in the removal of a sheath assembly 106, 146, 178, 214 from an endoscope insertion member (not separately labeled). A tear string 190, 228 is manually grasped and pulled to sever or rip the respective sheath 112, 152, 180, 216 along a straight or curved line extending at least a substantial portion of the length of the endoscope insertion member. The rip or tear in the sheath 112, 152, 180, 216 is preferably formed in a direction from the proximal end to the distal end of the instrument.

A sheath as discussed hereinabove with reference to the drawing figures, provides the benefit of keeping the endoscope relatively free from contact with the patient's body fluids or fecal material. The sheath is preferably a rectangular sheet made of a thin flexible material that is split from its proximal end to the distal end or to a point close to the distal end. One side of the split line has a permanent adhesive component that sufficiently overlaps the other side of the sheath to enable fixation of the sheath to an endoscope insertion member. Accordingly, the sheath sheet has a width greater than a circumference of an endoscope insertion member. The adhesive can be covered by a removable protective strip that is simply peeled off to expose the adhesive layer. The sheath is then wrapped width-wise over and completely about the endoscope and adhered to the non-adhesive side of the sheath, making a secure and fluid tight bond the entire length of the sheath. In order to easily apply a long and narrow sheath in accordance with the invention to an endoscope, the non-adhesive part of the sheath is first lightly bonded to the insertion shaft of the endoscope by means of a light-adhesive region also covered by a removable protective strip. Only once the first side is lightly bonded to the endoscope is the strip overlying the permanent glue remove. That side is then folded over the first side and permanently attached as described above. The sheath also contains an embedded tear-strip with a small portion of the tear-strip exposed, e.g., at the proximal end of the sheath, so as to facilitate grabbing of the tear strip and pulling it lengthwise down the sheath causing the sheath to easily split and be safely, cleanly and easily removed from the endoscope.

The distal end of the sheath is provided or associated with an end cap in the shape of a short tube that incorporates a transparent end portion that fits over the distal end of the endoscope insertion shaft, allowing for use of the endoscope's visualization capabilities and potentially the working channels of the endoscope.

Although the invention has been described in terms of particular embodiments and applications, one of ordinary skill in the art, in light of this teaching, can generate additional embodiments and modifications without departing from the spirit of or exceeding the scope of the claimed invention. For example, a sheath might be provided with only a single region of adhesive that serves to bond part of the sheath to an underlying portion of the sheath placed in direct contact with an endoscope insertion member. Although a tear string is preferably incorporate into a sheath, the tear string may be omitted where some other means of sheath removal is provided.

It is to be noted that a tear string or tensile member as those terms are used herein may cover a string, a wire, a reinforced, strengthened or thickened area of the sheath, etc.

Accordingly, it is to be understood that the drawings and descriptions herein are proffered by way of example to facilitate comprehension of the invention and should not be construed to limit the scope thereof.

What is claimed is:

1. An endoscope sheath assembly comprising a web member provided with an embedded tensile element for enabling a severing of said web member in preparation for removal of said web member from an endoscope insertion member, said web member being a rectangular sheet having a width greater than a circumference of said endoscope insertion member and provided in a region along a longitudinal edge with a layer of adhesive material to enable a fastening of said sheet to the endoscope insertion member upon a wrapping of the sheet completely about the endoscope insertion member.

2. The sheath assembly defined in claim 1, further comprising at least one releasable protective cover strip removably attached to the adhesive layer of said region.

3. The sheath assembly defined in claim 1, further comprising an end cap securable over a distal tip of said insertion member in a fluid tight engagement with said web member.

4. The sheath assembly defined in claim 1, further comprising an end cap secured to an end of said web member.

5. The sheath assembly defined in claim 1, wherein the adhesive material of said region is permanent adhesive.

6. The sheath assembly defined in claim 5 wherein said region is one region and said web member is provided in another region with a layer of adhesive material forming a separable bond.

7. The sheath assembly defined in claim 6 wherein said longitudinal edge is one longitudinal edge of said web member, said another region extending along an opposite longitudinal end of said web member.

8. The sheath assembly defined in claim 6 wherein said another region extends along a short or transverse edge of said web member.

9. The sheath assembly defined in claim 1 wherein an end cap is secured to a transverse edge of said sheet extending perpendicularly to said longitudinal edge.

10. The sheath assembly defined in claim 1 wherein said tensile element extends longitudinally along said web member.

11. The sheath assembly defined in claim 10 wherein said tensile element extends from one end of said web member to an opposite end of said web member.

12. The sheath assembly defined in claim 1 wherein said tensile element extends along a weakened region of said web member.

13. The sheath assembly defined in claim 1 wherein said web member is provided with a further layer of adhesive in a region along a short or transverse edge of said web member, further comprising an end cap securable to said web member via said further layer of adhesive.

14. The sheath assembly defined in claim 1 wherein said web member is provided with at least one channel.

15. A medical method comprising:

providing an endoscope insertion member;

providing a web or sheet having a width greater than a circumference of said endoscope insertion member;

wrapping said web or sheet width-wise about at least a distal end portion of said insertion member to form a sheath;

adhesively fastening said sheath about said insertion member;

inserting said insertion member with the sheath wrapped thereabout into a patient; and subsequently removing said insertion member with the sheath wrapped thereabout from the patient.

16. The method defined in claim 15 wherein the fastening of said sheath includes removing at least one protective cover strip from said web or sheet to uncover at least one adhesive region and subsequently pressing said adhesive region against said insertion member.

17. The method defined in claim 15, further comprising providing an end cap and attaching said end cap to a distal tip of said insertion member prior to inserting of said insertion member and said sheath into the patient, said end cap being also inserted into the patient.

18. The method defined in claim 15 wherein the wrapping of said sheath includes:

providing a cradle member having a groove;

placing said web or sheet over said cradle member so that a portion of said web or sheet lies in said groove;

disposing said endoscope insertion member on the portion of said web or sheet lying in said groove; and winding a side portion of said web or sheet about said endoscope insertion member after the disposing thereof on said web or sheet.

19. The method defined in claim 15 wherein the fastening of said sheath to said endoscope insertion member includes:

adhesively securing a first longitudinal edge region of said web or sheet to an outer surface of said endoscope insertion member; and subsequently adhesively securing a second longitudinal edge region of said web or sheet to an outer surface of said web or sheet.

20. The method defined in claim 15, further comprising:

after the removal of the insertion member and the sheath from the patient, pulling a tear string embedded in said sheath to sever said sheath along a predetermined line; and after the pulling of the tear string, separating the insertion member and the torn or severed sheath from one another.

21. The method defined in claim 20 wherein said tear string is disposed along a weakened region of said sheath, the pulling of said tear string severing said sheath along said weakened region.

22. An endoscope sheath assembly comprising a sheet having a longitudinal edge and a width greater than a circumference of an endoscope insertion member, said sheet being provided in a region along the longitudinal edge with a layer of adhesive material to enable a fastening of said sheet to the endoscope insertion member upon a wrapping of the sheet completely about the endoscope insertion member to sheath the endoscope insertion member.

* * * * *